United States Patent [19]
Jacobs

[11] Patent Number: 4,974,603
[45] Date of Patent: Dec. 4, 1990

[54] NEEDLE EJECTOR APPARATUS FOR A BLOOD SAMPLE VACUUM TUBE CONTAINER

[76] Inventor: Jerome Jacobs, 6415 Allison Rd., Miami Beach, Fla. 33141

[21] Appl. No.: 445,243

[22] Filed: Dec. 4, 1989

[51] Int. Cl.⁵ .............................................. A61B 5/00
[52] U.S. Cl. ................................... 128/763; 128/919; 604/198
[58] Field of Search .............. 128/760, 763, 770, 919; 604/59, 181, 188, 197, 198, 199, 263

[56] References Cited
U.S. PATENT DOCUMENTS

| | | | |
|---|---|---|---|
| 4,822,343 | 4/1989 | Beiser | 128/763 |
| 4,840,185 | 6/1989 | Hernandez | 128/763 |
| 4,841,985 | 6/1989 | Wanamaker | 128/763 |

FOREIGN PATENT DOCUMENTS 2564726 11/1985 France ................................ 128/763

Primary Examiner—Max Hindenburg
Attorney, Agent, or Firm—Malloy, Downey & Malloy

[57] ABSTRACT

A needle ejector apparatus to be used for removing a needle from a blood sample vacuum tube container, the apparatus being structurally adapted to receive a vacuum tube container and attached needle therein whereupon the downward depression of a push rod on the apparatus causes an engaging means to grasp a rubber cap on the needle located within the interior of the vacuum tube container. Further depression of the push rod causes rotation of a head structure and attached engaging means thereby enabling separation and ejection of the needle from the vacuum tube container after use without the necessity of the needle being touched by medical personnel. Danger of contamination by inadvertent puncture when removing the needle from the vacuum tube container is thereby eliminated.

12 Claims, 2 Drawing Sheets

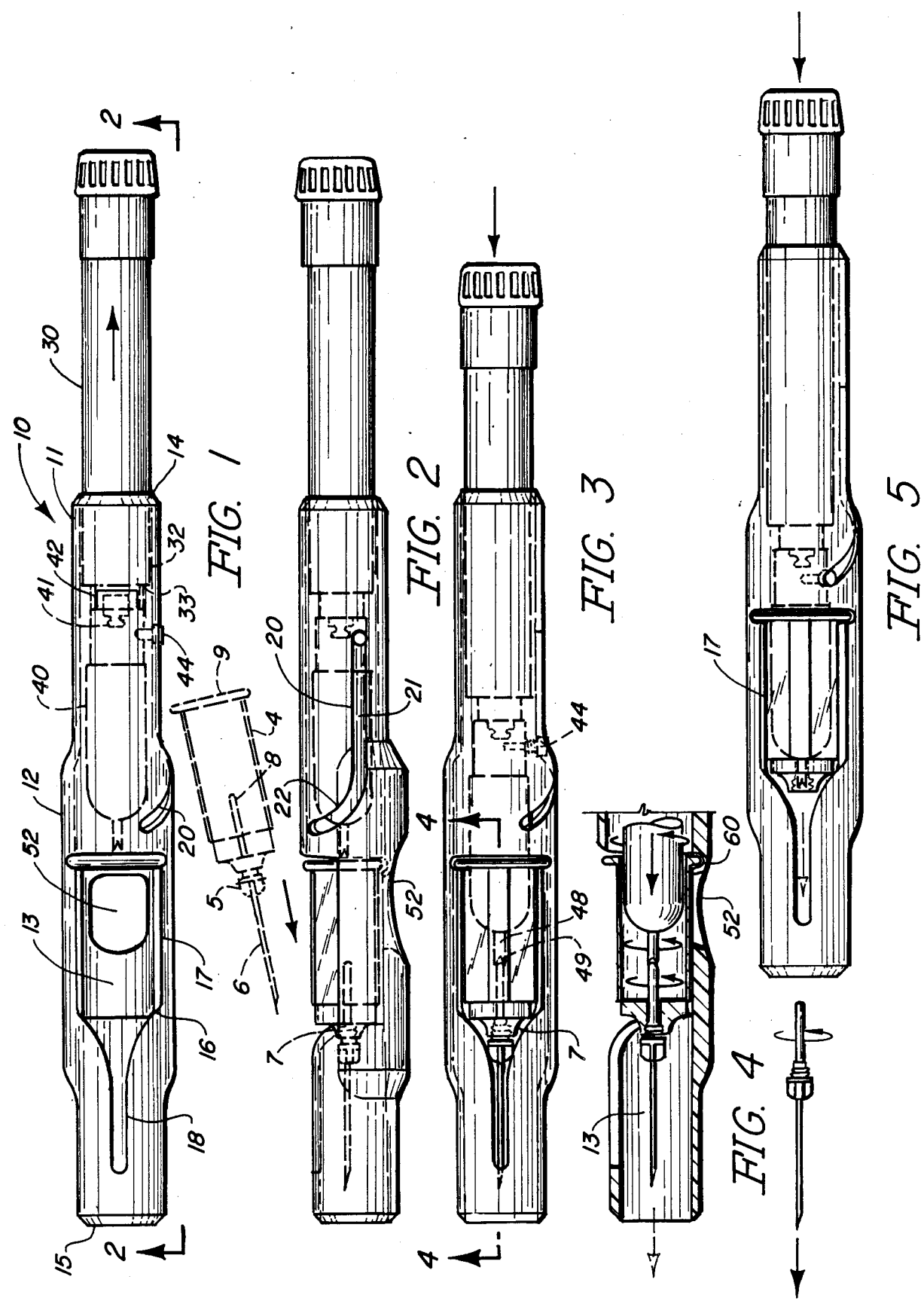

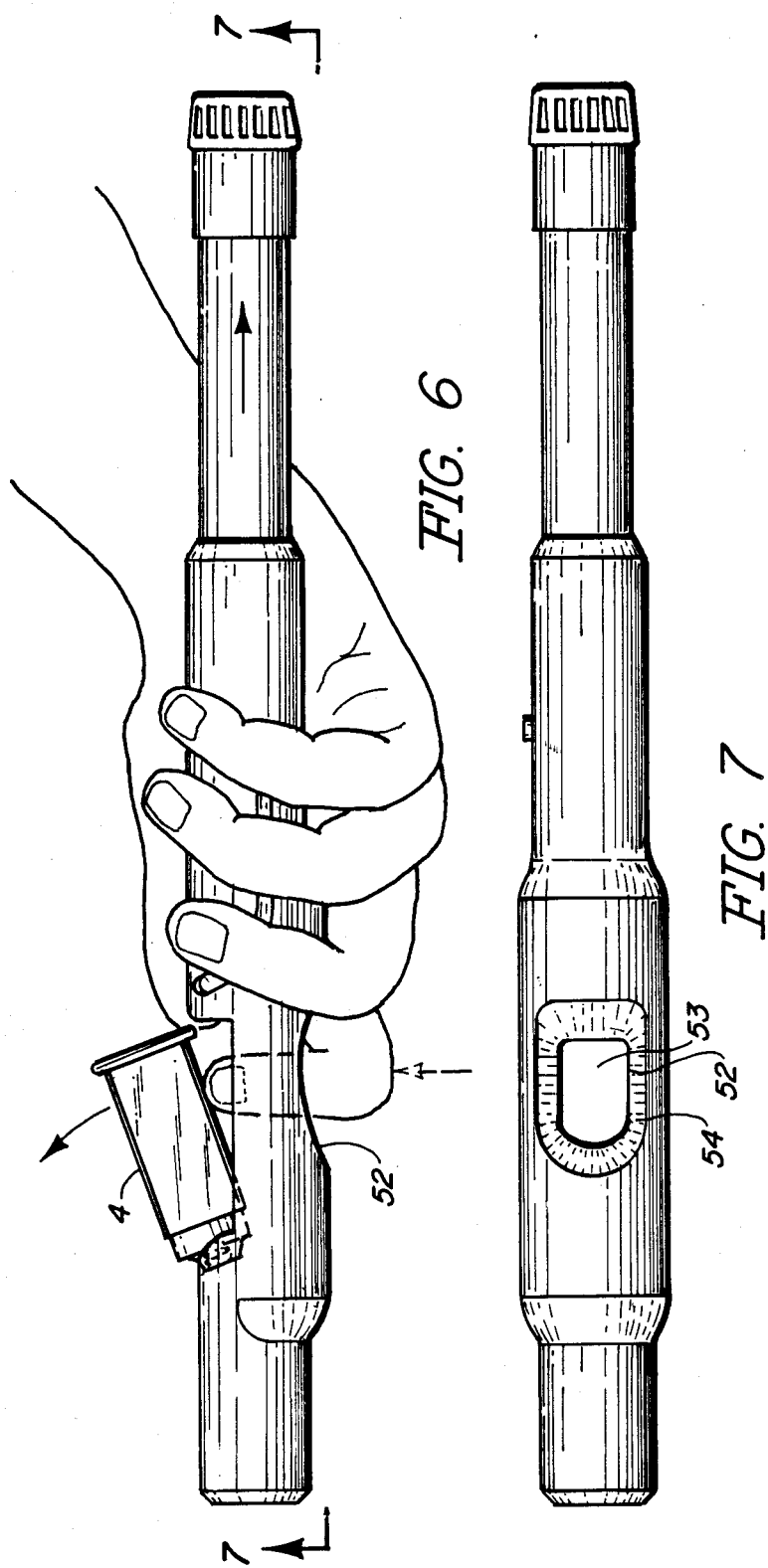

NEEDLE EJECTOR APPARATUS FOR A BLOOD SAMPLE VACUUM TUBE CONTAINER

BACKGROUND OF THE INVENTION

1. Field of the Invention

A needle ejector apparatus is structurally adapted to receive a used vacuum tube container and attached needle therein and is specifically designed to accomplish separation of the needle from the vacuum tube container after use with blood sample vacuum tubes without necessitating the handling of the needle or the end of the vacuum tube to which the needle is threadably secured.

2. Description of the Prior Art

The use of vacuum tube containers with attached needles in combination with vacuum tubes for extracting blood from a patient for sampling and analysis is extremely widespread and a common practice in the medical field. In use, the needle on the vacuum tube container is inserted into a vein of a patient, most commonly along the arm, in such a manner so that the distal end of the needle is disposed within the interior of the vein in confronting relation to the flow of blood. An opposite end of the needle is disposed within the interior of the vacuum tube container and is covered with a rubber cap for sanitary purposes. To extract blood, a sealed vacuum tube is inserted into the vacuum tube container whereupon placing pressure on the vacuum tube causes the needle to penetrate the rubber cap and in turn, the seal on the vacuum tube as the end of the needle enters the interior of the tube. The vacuum within the tube causes blood to be drawn from the patient's vein through the needle and into the tube. The vacuum tube can then be removed, and a subsequent vacuum tube placed within the container to allow the attending physician to take a second sampling of blood. In this manner, numerous samples of blood can be taken through the same needle without the need of inserting a number of needles into a patient's arm. Presently, in the existing art, when sampling is completed with a particular patient, the needle and vacuum tube container are removed from the patient's arm and discarded. It is relatively simple to remove the needle from the vacuum tube container by simply unscrewing a threaded hub portion which secures the needle to the container. However, with the recent threat of the spread of Aids and other dangerous communicable diseases, it has become unlawful to handle any portion of the needle after it has been used to extract blood from a patient. Therefore, when blood sampling has been completed with a particular patient, the needle is left intact on the vacuum tube container and the entire assembly is discarded. While it is not unlawful to handle or reuse the vacuum tube container itself, because of the difficulty in separating the needle and container without handling any portion of the needle, physicians and other medical personnel have found it easiest to simply discard the entire needle and vacuum tube container assembly after each use.

It is common practice for a large medical facility to dispose of hundreds of these needle and vacuum tube container assemblies each day. The loss incurred from having to dispose of the container portion after each use can be quite substantial when calculated over a long period of time. While it is highly desirous and advantageous to remove the needle from the vacuum tube container in order to permit reuse of the container, the difficulty in removing the needle without actually handling it has discouraged most medical personnel from doing so.

Accordingly, there is a need in the medical industry as well as the associated instrument industry for an apparatus or device capable of effectively separating or ejecting the needle from the vacuum tube container subsequent to use thereof without requiring handling of the needle or touching any exterior surface surrounding the threaded hub portion thereof. Such an apparatus should be capable of unscrewing the needle and threaded hub portion from the threaded end of the vacuum tube container whereby a new needle can then be threadably attached to the vacuum tube container for the next use.

SUMMARY OF THE INVENTION

The present invention is directed towards an apparatus of the type used with a conventional vacuum tube container and attached needle for the separation and/or ejection of a used, contaminated needle from the threaded end of the container thereof without requiring a person to come into direct contact with the needle or its connecting hub portion which threadably secures the needle to the vacuum tube container.

The needle ejector apparatus of the present invention comprises a hollow tubular body portion having an elongated configuration and being structured and configured to adaptably receive a push rod in telescopic relation thereof. The push rod is specifically dimensioned so as to have a diameter slightly less than that of the interior of the tubular body portion thereby allowing the push rod to be telescopically extended and depressed within the hollow interior of the tubular body. The tubular body includes a receiving slot to allow passage of a vacuum tube container and attached needle therethrough. In this manner, the vacuum tube container and needle are seated within the hollow interior of the tubular body and extending along its length thereof. The push rod includes a proximal end which is fitted with a rotating head and attached engaging means. Extending from a side of the rotating head, there is a guide pin which is specifically dimensioned to fit within a curvilinear track along a portion of the length of the tubular body. Upon depression of the push rod, the guide pin travels along a relatively straight portion of the curvilinear track before coming to a curved portion extending partially around the circumference of the tubular body. Travel of the guide pin around the curved portion of the curvilinear track causes rotation of the head and attached engaging means simultaneous to the travel of the guide pin in the curvilinear track, the engaging means and head on the push rod enter through an open end of the vacuum tube container whereupon the engaging means surrounds and grasps a rubber cap fitted to an end of the needle. As the head portion begins to rotate, the needle being under the grasp of the engaging means is rotated to effectively unscrew the hub portion of the needle from the threaded end of the container. Further rotation of the head and engaging means causes the needle to be separated and ejected from the vacuum tube container whereupon the needle exits the tubular body through an open end thereof. After ejection of the needle, the vacuum tube container can be easily removed from the receiving slot in the interior of the tubular body by simply inserting a finger through a window portion and forcing the container out from its seated position within the receiving slot.

The invention accordingly comprises the features of construction, combination of elements and arrangement of parts which will be exemplified in the construction hereinafter set forth and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is a top plane view of the needle ejector apparatus.

FIG. 2 is a side plane view of the needle ejector apparatus illustrating the insertion of a vacuum tube container and attached needle into its seated position within the receiving slot.

FIG. 3 is a top plane view of the present invention showing the vacuum tube container within the receiving slot and the push rod partially depressed.

FIG. 4 is a side sectional view in partial cut-away showing the engagement of the engaging means with the needle and rotation of the head to effect ejection of the needle.

FIG. 5 is a top plane view of the present invention showing full depression of the push rod and ejection of the needle.

FIG. 6 is a perspective view illustrating the removal of the vacuum tube container from the receiving slot.

FIG. 7 is a bottom plane view of the present invention illustrating the extracting means along the tubular body.

Like reference numerals refer to like parts throughout the several views of the drawings.

DETAILED DESCRIPTION OF THE PREFERRED EMBODIMENT

The present invention is illustrated in FIGS. 1 through 7 and comprises a needle ejector apparatus for removing a needle from a vacuum tube container as commonly used during the taking of blood samples. As will be explained in greater detail hereinafter, the needle ejector apparatus 10 is specifically designed for use in combination with a conventional, prior art vacuum tube container 4 and attached needle 6, and is specifically designed to facilitate the removal of the needle 6 from the container 4. FIG. 1 illustrates a preferred embodiment of the present invention wherein the needle ejector apparatus 10 includes an elongated tubular body 11 having an increased diameter portion 12 extending partially along its length. The tubular body 11 further includes a hollow interior 13, as shown in FIGS. 1 and 4, with a first open end 14 and a second open end 15. A receiving slot 16 is formed within the increased diameter portion 12 and includes a container receiving portion 17 and a needle receiving portion 18 specifically configured to allow the vacuum tube container 4 and attached needle 6 to pass transversely therethrough whereupon the container and needle are seated within the hollow interior 13 of the tubular body 11 extending along a common axis thereof.

The tubular body 11 includes a curvilinear track 20 extending partially along its length from a point in spaced relation to the first end 14 and terminating at a point in close spaced relation to the receiving slot 16. The curvilinear track 20 includes a substantially straight portion 21 extending from the increased diameter portion 12 to a point in spaced relation to the end 14. The curvilinear track 20 further includes a curved portion 22 extending from the straight portion 21 towards the receiving slot 16 and partially around the circumference of the increased diameter portion 12.

A push rod 30 extends from the end 14 of the tubular body 11 and is dimensioned and configured to fit within the hollow interior 13 of the tubular body 11 as at 32, thereby permitting extension and depression of the push rod 30 in telescopic relation to the tubular body. Attached to an end 33 of the push rod 30 within the hollow interior of the tubular body is a rotatable head 40. The rotatable head 40 is attached to the push rod 30 by a pivot pin 41 which is rotatably mounted within a bearing structure 42 attached to the end 33 of the push rod 30, the pivot pin 41 extending from the bearing and being fixedly mounted within the head 40 in such a manner as to permit rotation of the head relative to the push rod 30.

A guide pin 44 extends from a side of the head 40 in transverse relation to its axis thereof. The guide pin 44 is fitted within the curvilinear track 20 to permit travel along the length of the track 20 upon depression and extension of the push rod 30. Upon depression of the push rod 30, the guide pin 44 travels along the straight portion 21 of the curvilinear track 20 as the head 40 travels axially through the hollow interior of the tubular body towards the receiving slot 16. As the guide pin 44 travels around the curved portion 22 of the curvilinear track 20, the head 40 is forced to rotate in the direction of the transverse travel of the guide pin 44. An engaging means 48 extends from the distal end of the head portion in axial relation to the head 40 and push rod 30 thereof.

In use, a vacuum tube container 4 with attached needle 6 is inserted within the retaining slot of the tubular body 11, as illustrated in FIG. 2. The needle 6 is threadably connected to an end of the vacuum tube container as at 7 by means of a threaded hub portion 5 fixedly mounted around the needle 6 at a point substantially midway along the needle's length. Upon depression of the push rod 30, the head 40 and attached engaging means 48 travel through the hollow interior 13 of the tubular body 11 towards the receiving slot 16. The head 40 is specifically configured to pass through an open end 9 of the vacuum tube container when the container is seated within the receiving slot 16. As the head 40 passes into the interior of the vacuum tube container 4, the engaging means 48 engages the rubber cap 8 on the end of the needle 6 as shown at 49 in FIG. 4.

Upon further depression of the push rod, the guide pin 44 enters the curved portion 22 of the curvilinear track thereby causing the head 40 and attached engaging means 48 to rotate as illustrated in FIG. 5. As the head and attached engaging means rotate, the end 49 of the engaging means 48 grasps and surrounds the rubber cap 8 of the needle whereupon further rotation of the attached head 40 causes the needle to be unscrewed from its threaded attachment with the end of the vacuum tube container 4. Further depression of the push rod forces the needle 6 away from the vacuum tube container 4 and out of the hollow end 15 of the tubular body 11.

After removing the needle 6 from the vacuum tube container 4, the container 4 is removed from the receiving slot 16 by inserting a finger through the window 53 of the extracting means 52 whereupon the container is forced from its seated position in the receiving slot facilitating removal thereof, as illustrated in FIG. 6. The extracting means 52, as shown in FIG. 7, includes a beveled portion 54 formed in the increased diameter portion 12 of the tubular body 11 and in surrounding relation to the window 53 thereof.

Now that the invention has been described, What is claimed is:

1. For use on a vacuum tube container of the type used to support a blood sample vacuum tube, wherein the vacuum tube container includes a needle extending axially therefrom, said needle being threadably attached to and extending into the interior of the vacuum tube container;

a needle ejector apparatus comprising:

an elongate tubular body having a hollow interior and including a first end and a second end, said tubular body further including a receiving slot on a side thereof, said slot dimensioned and disposed to allow passage therethrough of the vacuum tube container and needle into and out of said hollow interior, said elongate tubular body further including a curvilinear track extending along a portion of the length of said tubular body between said first end and said receiving slot and having a curved portion extending partially around the circumference of said tubular body, a push rod extending from said first end of said tubular body, said push rod having a smaller diameter than the diameter of said hollow interior and telescopically extending into said hollow interior and being movable along a portion of the length of said tubular body, a head rotatably connected to a proximal end of said push rod within said hollow interior of said tubular body, said head being dimensioned to allow passage into an open end of the vacuum tube container when said push rod is depressed, a guide pin attached to said head and disposed within said curvilinear track and being dimensioned and configured to permit movement along the length of said curvilinear track during depression and extension of said push rod, needle engaging means fixedly secured to and extending axially from said head on said push rod, said needle engaging means dimensioned and configured to adaptably receive and grasp a rubber cap fitted to said needle within the vacuum tube container, extracting means disposed along said tubular body for extracting the vacuum tube container from said hollow interior, whereby the needle is separated and ejected from the vacuum tube container upon depression of said push rod into said hollow interior of said tubular body and engagement of said engaging means with said rubber cap and rotation of said engaging means and needle thereof.

2. An apparatus as in claim 1 wherein said receiving slot on said tubular body includes a container receiving portion having an open face of sufficient dimension to receive the vacuum tube container therein.

3. An apparatus as in claim 2 wherein said receiving slot further includes a needle receiving portion extending from said container receiving portion and having a sufficient width to allow transverse passage of the needle therethrough.

4. An apparatus as in claim 3 wherein the tubular body includes an increased diameter portion extending at least along the length of said container receiving portion.

5. An apparatus as in claim 1 wherein said needle engaging means includes a rod formed of a rigid material and having a hollow end sized and configured to fit securely around and grasp said rubber cap on the needle.

6. An apparatus as in claim 5 wherein said needle engaging means travels substantially through said hollow interior of said tubular body and at least along the length of said container receiving portion upon depression of said push rod.

7. An apparatus as in claim 3 wherein said container receiving portion includes a groove dimensioned and configured to receive a flanged edge around said vacuum tube container.

8. An apparatus as in claim 1 wherein said push rod includes a cap fixedly secured to a distal end thereof, said cap including a grip portion extending substantially around an outer exposed surface.

9. An apparatus as in claim 1 wherein said head is rotatably connected to said push rod by a pivot pin, said pivot pin extending axially between said head and said push rod.

10. An apparatus as in claim 9 wherein said push rod includes a bearing structure fitted to a proximal end thereof, said pivot pin fitted to and extending from said bearing structure and being rotatable in axial relation to said push rod.

11. An apparatus as in claim 10 wherein said guide pin is disposed perpendicular to said pivot pin and is fitted and disposed within said curvilinear track to cause rotation of said head upon travel around said curved portion thereof.

12. An apparatus as in claim 1 wherein said extracting means includes a window disposed along said tubular body and opposite to said receiving slot and being dimensioned and configured to permit insertion of a finger to force the vacuum tube container out from within the hollow interior of said tubular body.

* * * * *